(12) United States Patent
Taft et al.

(10) Patent No.: US 8,114,883 B2
(45) Date of Patent: Feb. 14, 2012

(54) POLYMER FORMULATIONS FOR DELIVERY OF BIOACTIVE MATERIALS

(75) Inventors: David Taft, Atherton, CA (US); Stelios Tzannis, Newark, CA (US); Wei-Guo Dai, Sunnyvale, CA (US); Sandra Ottensmann, Mountain View, CA (US); Steven Bitler, Menlo Park, CA (US); Qiang Zheng, Palo Alto, CA (US); Adam Bell, Pacifica, CA (US)

(73) Assignee: Landec Corporation, Menlo Park, CA (US)

( * ) Notice: Subject to any disclaimer, the term of this patent is extended or adjusted under 35 U.S.C. 154(b) by 230 days.

(21) Appl. No.: 12/287,520

(22) Filed: Oct. 10, 2008

(65) Prior Publication Data

US 2009/0209558 A1    Aug. 20, 2009

Related U.S. Application Data

(60) Provisional application No. 61/005,400, filed on Dec. 4, 2007, provisional application No. 61/131,123, filed on Jun. 4, 2008, provisional application No. 61/131,716, filed on Jun. 10, 2008.

(51) Int. Cl.
*A61K 31/519* (2006.01)
*A61K 31/196* (2006.01)

(52) U.S. Cl. .................................. 514/259.41; 514/567

(58) Field of Classification Search .................. None
See application file for complete search history.

(56) References Cited

U.S. PATENT DOCUMENTS

| | | | |
|---|---|---|---|
| 3,608,549 A | 9/1971 | Merrill | |
| 4,558,690 A | 12/1985 | Joyce | |
| 4,830,855 A | 5/1989 | Stewart | |
| 5,120,349 A | 6/1992 | Stewart | |
| 5,129,180 A | 7/1992 | Stewart | |
| 5,143,730 A | 9/1992 | Fues et al. | |
| 5,156,911 A | 10/1992 | Stewart | |
| 5,213,808 A | 5/1993 | Bar-Shalom et al. | |
| 5,308,623 A | 5/1994 | Fues et al. | |
| 5,384,333 A | 1/1995 | Davis et al. | |
| 5,387,450 A | 2/1995 | Stewart | |
| 5,412,035 A | 5/1995 | Schmitt et al. | |
| 5,429,654 A | 7/1995 | Swarup | |
| 5,469,867 A | 11/1995 | Schmitt | |
| 5,662,711 A | 9/1997 | Douglas | |
| 5,665,822 A | 9/1997 | Bitler | |
| 5,687,718 A | 11/1997 | Fischer et al. | |
| 5,725,881 A | 3/1998 | Buchholz et al. | |
| 5,783,302 A | 7/1998 | Bitler | |
| 5,826,584 A | 10/1998 | Schmitt | |
| 5,852,117 A | 12/1998 | Schoenberg et al. | |
| 5,895,404 A | 4/1999 | Ruiz | |
| 5,945,457 A | 8/1999 | Plate et al. | |
| 6,001,395 A | 12/1999 | Coombes et al. | |
| 6,004,549 A | 12/1999 | Reichert et al. | |
| 6,199,318 B1 | 3/2001 | Stewart | |
| 6,214,901 B1 | 4/2001 | Chudzik | |
| 6,224,793 B1 * | 5/2001 | Hoffman et al. ............... 264/4.1 |
| 6,255,367 B1 | 7/2001 | Bitler | |
| 6,297,337 B1 | 10/2001 | Marchant et al. | |
| 6,319,521 B1 | 11/2001 | Randolph | |
| 6,344,035 B1 | 2/2002 | Cudzik | |
| 6,352,667 B1 | 3/2002 | English | |
| 6,423,345 B2 | 7/2002 | Bernstein et al. | |
| 6,469,133 B2 | 10/2002 | Baker et al. | |
| 6,524,274 B1 | 2/2003 | Rosenthal | |
| 6,528,080 B2 | 3/2003 | Dunn et al. | |
| 6,540,984 B2 | 4/2003 | Stewart | |
| 6,569,128 B1 | 5/2003 | Christensen et al. | |
| 6,576,254 B1 | 6/2003 | Uchegbu | |
| 6,653,395 B1 | 11/2003 | Bergstrom et al. | |
| 6,656,385 B2 | 12/2003 | Lynch | |
| 6,657,042 B2 | 12/2003 | Rafler et al. | |
| 6,699,952 B2 | 3/2004 | Chaikof | |
| 6,730,322 B1 | 5/2004 | Berstein et al. | |
| 6,780,930 B2 | 8/2004 | Lewis | |
| 6,831,116 B2 | 12/2004 | Bitler | |
| 6,858,634 B2 | 2/2005 | Asrar et al. | |
| 6,866,860 B2 | 3/2005 | Nathan | |
| 6,887,960 B2 | 5/2005 | Parker et al. | |
| 6,890,583 B2 | 5/2005 | Chudzik | |
| 6,951,642 B2 | 10/2005 | Scholz et al. | |
| 6,964,778 B1 | 11/2005 | Hui | |
| 6,967,234 B2 * | 11/2005 | Nathan ........................ 528/272 |
| 6,989,417 B2 | 1/2006 | Bitler et al. | |
| 7,008,667 B2 | 3/2006 | Chudzik | |
| 7,030,084 B2 | 4/2006 | Ekwuribe et al. | |
| 7,083,572 B2 | 8/2006 | Unger et al. | |
| 7,220,430 B2 | 5/2007 | Ishibashi et al. | |

(Continued)

FOREIGN PATENT DOCUMENTS

EP    0064379 A1    11/1982

(Continued)

OTHER PUBLICATIONS

Tuncay, IntJPharm, 195, 2000.*

(Continued)

*Primary Examiner* — Robert A Wax
*Assistant Examiner* — William Craigo
(74) *Attorney, Agent, or Firm* — James S. McDonald

(57) ABSTRACT

Delivery of drugs in association with PLGA polymers which have crystallinity resulting from the presence of long chain alkyl groups in terminal units.

40 Claims, 6 Drawing Sheets

U.S. PATENT DOCUMENTS

| | | | |
|---|---|---|---|
| 2002/0106406 | A1 | 8/2002 | McHugh et al. |
| 2002/0114827 | A1 | 8/2002 | Zhang |
| 2002/0161437 | A1 | 10/2002 | Zhou et al. |
| 2003/0082217 | A1 | 5/2003 | Afriat |
| 2003/0224974 | A1 | 12/2003 | Bolotin |
| 2004/0009229 | A1* | 1/2004 | Unger et al. ............... 424/486 |
| 2004/0052746 | A1 | 3/2004 | Tamareselvy |
| 2004/0117006 | A1 | 6/2004 | Lewis et al. |
| 2004/0208844 | A1 | 10/2004 | Ignatious |
| 2004/0236013 | A1 | 11/2004 | Lewis |
| 2004/0254419 | A1 | 12/2004 | Wang et al. |
| 2005/0019923 | A1 | 1/2005 | Uchegbu et al. |
| 2005/0169977 | A1 | 8/2005 | Kanios et al. |
| 2005/0197251 | A1 | 9/2005 | Ding et al. |
| 2005/0249697 | A1 | 11/2005 | Uhrich et al. |
| 2005/0249799 | A1 | 11/2005 | Jacob |
| 2006/0018948 | A1 | 1/2006 | Guire |
| 2006/0024361 | A1 | 2/2006 | Odidi |
| 2006/0034891 | A1 | 2/2006 | Lawin et al. |
| 2006/0148982 | A1 | 7/2006 | Uchegbu et al. |
| 2006/0167116 | A1 | 7/2006 | Uchegbu et al. |
| 2006/0286064 | A1 | 12/2006 | Turnell et al. |
| 2006/0292222 | A1 | 12/2006 | Jonasee |
| 2007/0016284 | A1 | 1/2007 | Pacetti |
| 2007/0023226 | A1 | 2/2007 | Hawash et al. |
| 2007/0134310 | A1 | 6/2007 | Nedberge et al. |
| 2007/0142461 | A1 | 6/2007 | Baker et al. |
| 2007/0259584 | A1 | 11/2007 | Whitehouse |
| 2009/0124996 | A1 | 5/2009 | Heneveld et al. |
| 2009/0177158 | A1 | 7/2009 | Krumme |
| 2009/0198183 | A1 | 8/2009 | Krumme |
| 2009/0240200 | A1 | 9/2009 | Heneveld et al. |

FOREIGN PATENT DOCUMENTS

| | | |
|---|---|---|
| EP | 0568345 A1 | 11/1993 |
| EP | 0778304 | 6/1997 |
| EP | 1348451 A1 | 10/2003 |
| EP | 1430916 A1 | 6/2004 |
| EP | 1629835 A1 | 3/2006 |
| GB | 2160100 A | 12/1985 |
| GB | 2161819 A | 1/1986 |
| JP | 62042918 A | 2/1987 |
| JP | 3123730 A | 5/1991 |
| JP | 2002 138 033 A | 5/2002 |
| RU | 2092161 | 10/1997 |
| WO | WO 92/13901 | 8/1992 |
| WO | WO 94/07940 A1 | 4/1994 |
| WO | WO 96/18417 A1 | 6/1996 |
| WO | WO 99/36058 | 7/1999 |
| WO | WO 99/47543 A2 | 9/1999 |
| WO | WO 99/56731 | 11/1999 |
| WO | WO 91/04015 A1 | 4/2001 |
| WO | WO 01/54671 A1 | 8/2001 |
| WO | WO 01/87276 | 11/2001 |
| WO | WO 02/45685 A2 | 6/2002 |
| WO | WO 03/022323 A1 | 3/2003 |
| WO | WO 03/028653 | 4/2003 |
| WO | WO 03/033027 | 4/2003 |
| WO | WO 2004/024779 | 3/2004 |
| WO | WO 2004/026912 | 4/2004 |
| WO | WO 2004/052339 | 6/2004 |
| WO | WO 2005/051358 A1 | 6/2005 |
| WO | WO 2005/084639 | 9/2005 |
| WO | WO 2006/039152 | 4/2006 |
| WO | WO 2006/128471 A2 | 12/2006 |
| WO | PCT/US07/023226 | 6/2008 |
| WO | WO 2008/066657 A2 | 6/2008 |

OTHER PUBLICATIONS

Amsden, "Development of Biodegradable Injectable Thermoplastic Oligomers" Biomacromolecules 2004, vol. 5, pp. 637-642.

U.S. Appl. No. 60/856,430, filed May 3, 2008, Schmitt.

U.S. Appl. No. 60/857,546, filed May 8, 2008, Schmitt.

U.S. Appl. No. 60/857,755, filed May 8, 2008, Krumme.

U.S. Appl. No. 60/964,066, filed Feb. 8, 2009, Krumme.

U.S. Appl. No. 60/993,541, filed Mar. 12, 2009, Krumme.

U.S. Appl. No. 61/016,223, filed Jun. 21, 2009, Krumme.

Lee, J. et al, "Thermosenstive Permeation From Side-Chain Crystalline Ionomers", Journal of Polymer Science: Part B: Polymer Physics, vol. 38, pp. 823-830; 2000.

Mohr, J.M., et al., "Drug Delivery with Side Chain Crystallizable Polymer Blends", 1991; Proceedings of the 18$^{th}$ International Symposium on Controlled Release of Bioactive Materials, pp. 409-410; Controlled Release Society, U.S.A.

Mohr, J.M., et al, "Pulsatile Transdermal Drug Delivery", 1992; Proceedings of the 19$^{th}$ International Symposium on Controlled Release of Bioactive Materials, pp. 377-378; Controlled Release Society, U.S.A.

Brannon-Peppas, L., "Polymers in Controlled Drug Delivery", Medical Plastics and Biomaterials, p. 34, Nov. 1997.

Birnbaum, D., et al., "Microparticle Drug Delivery Systems" Drug Delivery Systems in Cancer Therapy, Chapter 6, pp. 117-135; Sep. 2003.

Du, J., et al., "pH Sensitive Vesicles Based on a Biocompatible Zwitterionic Diblock Copolymer", Journal of American Chemistry Society, vol. 127, #51, pp. 17982-17983; 2005.

Kaneko, T.; Miyazaki, T.; Yamaoka, K.; Katayama, Y.; Matsuda, A.; Gong, J.; and Osada, Y.; "Shape-Memory Gels with Multi-Stimuli Responses"; Proceedings of SPIE, vol. 3669, pp. 199-208, Smart Structures and Materials; May 1999: Electroactive Polymer Actuators and Devices.

Wei, J-S.; Zeng, H-B.; Liu, S-Q.; Wang, X-G.; Tay, E.H.; and Yang, Y-Y.; Temperature and pH Sensitive Core-Shell Nanoparticles Self-Assembled From Poly(N-Isopropylacrylamide-Co-Acrylic Acid-CO-Cholesteryl Acrylate) for Intracellular Delivery of Anticancer Drugs; Sep. 2005; Frontiers in Bioscience 10, pp. 3058-3067; Frontier in Bioscience, U.S.A.

Ng, C.C.; Cheng, Y-L.; Saville, B.A.; Thermoresponsive Polymer Membrane for the Local Delivery of Drugs; Summer 2001; Journal of Sexual and Reproductive Medicine, vol. 1 #1, pp. 21-27; Pulses Group Inc., Canada.

Luppi, B.; Cerchiara, T.; Bigucci, F.; Orienti, I.; and Zecchi, V.; pH-Sensitive Polymeric Physical-Mixture for Possible Site-Specific Delivery of Ibuprofen; Mar. 2003; European Journal of Pharmaceutics and Biopharmaceutics, 55, #2, pp. 199-202; Elsevier, Netherlands.

Bulmus, V.; Woodward, M.; Lin, L.; Murthy, N.; Stayton, P.; and Hoffman, A.; A New pH Responsive and Glutathione-Reactive, Endosomal Membrane Disruptive Polymeric Carrier for Intracellular Delivery of Biomolecular Drugs; Dec. 2003; Journal of Controlled Release, vol. 93, #2, pp. 105-120; Elsevier, Netherlands.

K.M. Scholsky and R.M. Fitch; Controlled Release of Pendant Bioactive Materials from Acrylic Polymer Colloids; 1986; Journal of Controlled Release, vol. 3, #1-4, pp. 87-102; Elsevier, Netherlands.

LaVan, D.A.; McGuire, T.; and Langer, R.; Small Scale Systems for in Vivo Drug Delivery; Oct. 2003; Nature Biotechnology, vol. 21, #10, pp. 1184-1191; Nature Publishing Group., U.K.

Schmidt, E.E.; Mohr, J.; and Stewart, R.F.; Side Chain Crystallizable Polymer Based Drug Delivery Phenomenon; 1991; in Proceedings of the 18$^{th}$ International Symposium on Controlled Release of Bioactive Materials, p. 134-135; Controlled Release Society, U.S.A.

Torchilin, V., "Structure and Design of Polymeric Surfactant-Based Drug Delivery Systems", Journal of Controlled Release, vol. 73, #2-3, pp. 137-172; Jun. 2001.

Boudreaux, C.J., et al., "Controlled Activity Polymers. XI Hydrolytic Release Studies of Hydrophilic Copolymers With Labile Esters of Model Allelopathic Phenols", Journal of Controlled Release, vol. 44, #2-3, pp. 185-194, Feb. 1997.

Loth, H., et al. "Methoxy-Polyethoxy Side-Chain Silastomers as Materials Controlling Drug Delivery by Diffusion Flux", Journal of Controlled Release, vol. 54, #3, pp. 273-282 Aug. 1998.

Yadav, S.K., et al., "Release Rates From Semi-Crystalline Polymer Microcapsules Formed by Interfacial Polycondensation", Journal of Membrane Science, vol. 125, #2, pp. 213-218; Mar. 1997.

Greene, L., "Side-Chain Crystallizable Polymers for Temperature-Activated Controlled Release", Polymeric Delivery Systems: Properties and Applications (ACS Symposium Series, No. 520), pp. 244-256, 1993.

Yu, L., et al., "A Subtle End-Group Effect on Macroscopic Physical Gelation of Triblock Copolymer Aqueous Solutions", Angew. Chem. Int. Ed. 2006, 45, 2232-2235.

Abayashinghe, N., et al., "Oligoethylene-End-Capped-Polylactides", Journal of Polymer Science: Part A: Polymer Chemistry, vol. 43, 5257-5266 (2005).

Mehvar, R., "Modulation of the Pharmacokinetics and Pharmacodynamics of Proteins by Polyethylene Glycol Conjugation", J. Pharm. Pharmaceut. Sci. 3(1):125-136, 2000.

Jiang, X., et al., ""Clickable" Polyglycolides: Tunable Synthons for Thermoresponsive, Degradable Polymers", Department of Chemistry, Michigan State University, East Lansing, MI, pp. 1-34.

Baker, G., et al., "New Polylactides from Hydroxyacids Derived from Renewable Sources". Polymer Preprints 2007, 48(2), 826.

Maruyama, S., et al., "A Synthetic Polymer, Poly(2-methacryloyloxyethyl phosphorylcholine-co-n-stearyl methacrylate), Stimulates Insulin Release form RINm5F Insulinoma Cells", Biosci. Biotechnol. Biochem., 68 (10), 2197-2200, 2004.

Pollino, J., et al., "Non-Covalent Side-Chain Polymers: Design Principles, Functionalization Strategies and Perspectives", Chem. Soc. Rev., 2005, 34, 193-207.

Roberts, M., et al., "Molecule Engineering Including Advanced PEGylation: Understanding the Full Potential", The Drug Delivery Companies Report Spring/Summer 2003, PharmaVentures, Ltd, 2003.

Ivan, B., et al., "New Nanophase Separated Intelligent Amphiphilic Conetworks and Gels", Macromolecular Symposia, Jul. 2005 vol. 227 (1), pp. 265-274, Wiley-VCH GmbH & Co. KgaA, Weinheim.

Shang, S., et al., "Comb-Like Ionomeric Copolymer: Itaconic Anhydride-co-Stearyl Methacrylate", ACS Polymer Preprints, 2007, vol. 48(2), pp. 871-872.

Davaran, S., et al., "Release of 5-Aminosalicylic Acid from Acrylic Type Polymeric Prodrugs Designed for Colon Drug Delivery", 1999; Journal of Controlled Release, 58, #3, pp. 279-287.

Bendix, Dieter, "Chemical Synthesis of Polyactide and its Copolymers for Medical Applications" 1998, Polymer Degradation and Stability, vol. 59, pp. 129-135; Elsevier Science Limited.

Mehta, Nozer M., "Oral Delivery and Recombinant Production of Peptide Hormones. Part I: Making Oral Delivery Possible" Jun. 2004 BIOPHARM International pp. 1-6.

Mehta, Nozer M., "Oral Delivery and Recombinant Production of Peptide Hormones. Part II: Recombinant Production of Therapeutic Peptides" Jul. 2004 BIOPHARM International pp. 7-9.

Morgan, V., "NOBEX: No Barriers" Overview. No date. File created Jun. 14, 2006; Nobex Corporation, Research Triangle Park, NC; 2 pp.

Quintana, A., et al., "Design and Function of a Dendrimer-Based Therapeutic Nanodevice Targeted to Tumor Cells Through the Folate Receptor" Pharmaceutical Research, vol. 19, #9, pp. 1310-1316; Sep. 2002.

Henry, C., "Cooking Cancer—Carbon Nanotubes and Near-Infrared Radiation Kill Cancer Cells by Heating" Chemical & Engineering News, vol. 83, #32, p. 16; 2005.

Yan, X., et al., "Cisplatin Delivery from Poly(acrylic acid-co-methyl methacrylate) Microparticles", Journal of Controlled Release, vol. 106, #12, pp. 198-208; Aug. 2005.

Nishino, S., et al. "Preparation and Interfacial Properties of a Novel Biodegradable Polymer Surfactant: Poly(ethylene oxide monooleate-*block*-DL-lactide)", Macromolecular Bioscience; vol. 5, pp. 1066-1073; 2005.

Anon. "Biodegradable Polymers: A Review" Environment and Plastics Industry Council (EPIC) Technical Report pp. 1-11; Nov. 24, 2000.

Anon. "What Are the Latest Drug Delivery Systems Made of?" Online Publication Science Scotland; The Royal Society of Edinburgh; Issue 2, pp. 9-10; Spring 2004.

Hadlington, S. "Special Delivery", "Chemistry World" (online edition, previously "Chemistry in Britain"), Royal Society of Chemistry, UK; No. 5, pp. 1-3; May 2003.

M. Dufresne et al.—Abstract—Preparation and characterization of water-soluble pH-sensitive nanocarriers for drug delivery Int. J. Pharmaceutics vol. 277, No. 1-2, 2004, pp. 81-90.

Emmanuel Roux et al. "Polymer based pH-sensitivecarriers as a means to improve the cytoplasmic delivery of drugs". Int. J. Pharmaceutics vol. 242, No. 1-2, 2002, pp. 25-36.

\* cited by examiner

POLYMER FORMULATIONS FOR DELIVERY OF BIOACTIVE MATERIALS

CROSS-REFERENCE TO RELATED APPLICATION

This application claims priority from and the benefit of (1) U.S. provisional Application No. 61/005,400, filed Dec. 4, 2007 (2) U.S. provisional Application No. 61/131,123, filed Jun. 4, 2008 and (3) U.S. provisional Application No. 61/131,716, filed Jun. 10, 2008. This application is related to (1) U.S. application Ser. No. 11/999,415, filed Dec. 4, 2007, which claims priority from and the benefit of U.S. provisional Application No. 60/873,234, filed Dec. 5, 2006 (2) International Application No. PCT/U.S. 2007/024909, filed Dec. 4, 2007, claiming priority from U.S. provisional Application No. 60/873,234, filed Dec. 5, 2006, and (3) International Application No. PCT/US 2007/025032, filed Dec. 5, 2007, claiming priority from U.S. provisional Application No. 60/873,234, filed Dec. 5, 2006. This application is also related to copending, commonly assigned application Ser. No. 12/284,755, filed Sep. 25, 2008. The entire disclosure of each of those applications is incorporated herein by reference for all purposes.

FIELD OF THE INVENTION

This invention relates to polymeric systems for the delivery of drugs.

BACKGROUND

There are many known polymeric systems for the delivery of drugs. A continuing problem is obtaining a desired loading and delivery profile at a desired location and at a desired time.

SUMMARY OF THE INVENTION

We have discovered, in accordance with the present invention, that useful delivery of drugs can be obtained through the association of drugs with certain polymers which are referred to herein as "ECC polymers" (ECC being an abbreviation for end cap crystalline).

The term "ECC polymer" is used in this specification to mean a polymer which
(A) comprises a plurality of polymeric molecules each of which consists essentially of
  (i) a polymer backbone which comprises a plurality of repeating units having the formula

—$CF^1F^2$—CO—O—     (1)

wherein
  $F^1$ is hydrogen and $F^2$ is hydrogen or methyl, the repeating units being the same or different, and
  (ii) at least one terminal unit which has the formula

-b—Cy     (2)

wherein
  Cy is an n-alkyl moiety containing 18-24 carbon atoms, and
  b is a bond or a moiety which has a valence of at least 2 and which links the Cy moiety to the polymer backbone, and which optionally contains one or more additional Cy moieties;
(B) has a crystalline melting temperature, Tp, of at least 35° C., optionally at least 40° C., an onset of melting temperature, To, such that the value of (Tp−To) is less than $Tp^{0.7}$, and a heat of fusion of at least 5 J/g, Tp, To and the heat of fusion being measured on a differential scanning calorimeter (DSC) as hereinafter described;
(C) has a number average molecular weight, Mn, measured as hereinafter described, of less than 10,000.

In ECC polymers containing more than one terminal unit of formula (2), and/or a terminal unit containing two or more Cy moieties, for example a total of 2, 3, 4 or 5 Cy moieties in one or more terminal units of formula (2), one or both of b and Cy can be the same or different in the different terminal units, and in a terminal unit containing more than one Cy moiety, the Cy moieties can be the same or different. A wide variety of such moieties are described below. The ECC polymer can optionally contain, in addition to the repeating units of formula (1) and one or more terminal units of formula (2), repeating units and/or terminal units having a different formula. Purely by way of example, the repeating units can be derived from a mixture of lactic acid and glycolic acid, and the polymer can contain two terminal units of formula (2), each containing at least one n-alkyl moiety containing 18 carbon atoms.

Purely by way of example, an ECC polymer can be prepared by endcapping a preformed PLGA by (i) reaction of the carboxyl end group of the PLGA with an alcohol containing a Cy moiety, e.g. stearyl alcohol or behenyl alcohol, or (ii) reaction of the carboxyl end group of the PLGA with a polyhydroxy compound, e.g. a sugar such as sorbitol, followed by esterification of one or more of the remaining hydroxy groups with a carboxylic acid (or the like) containing a Cy moiety, and/or (iii) by reaction of the hydroxyl end group with an n-alkyl carboxylic acid (or the like) in which the n-alkyl moiety contains 18-22 carbon atoms.

In a first aspect, this invention provides a pharmaceutical formulation which comprises an ECC polymer and a drug dispersed (uniformly on non-uniformly) in the polymer. The formulation may be, for example, sterile or sterilizable.

In a second aspect, this invention provides a method of treating a human being or other mammal which comprise administering a therapeutically effective amount of an ECC polymer and a drug to the mammal, the polymer and the drug being associated with each other in a pharmaceutical formulation before administration or becoming associated with each other during or after administration. The method may comprise subjecting the formulation to conditions which affect (i.e. decrease, increase or maintain substantially constant) the strength of the association between the drug and the polymer in at least part of the formulation, for example at an exposed surface of the formulation. Such methods can for example improve or preserve the health or appearance of, or assist in the diagnosis of, a human being or other animal.

In a third aspect, this invention provides a method of making a pharmaceutical formulation which comprises mixing a drug with an ECC polymer. In one such method, the drug has a maximum temperature to which it can be exposed without damage, and the drug is mixed with the polymer at a temperature at which the polymer is liquid (i.e. above Tp) and which is below the maximum temperature. Such mixing can for example be carried out in the absence of any liquid other than the polymer. In another method, the mixing is carried out in the presence of a liquid (which liquid may be a solvent for one or both or neither of the drug and the polymer). The liquid can be, for example, water, an aqueous solvent, a non-aqueous solvent (e.g. an aliphatic, aromatic or mixed aliphatic/aromatic organic solvent), a polar solvent, or a non-polar solvent. The ECC polymers can often be designed to melt over a relatively narrow temperature range and at a desired temperature. Furthermore, it is possible to obtain similar melting characteristics over a relatively wide range of molecular weight. Tp can for example be 40-70° C., 40-60° C., or 50-65° C. The melting point of a formulation comprising an ECC polymer and a drug will often be different from, generally lower than, the melting point of the ECC polymer.

BRIEF DESCRIPTION OF THE DRAWINGS

The invention is illustrated in the accompanying drawings, in which the Figures are graphs showing the total release of a drug (risperidone or diclofenac sodium) over time from a pharmaceutical formulation of the invention or, for comparison purposes, a similar formulation in which the polymer does not contain a Cy moiety.

DETAILED DESCRIPTION OF THE INVENTION

Figure 1A:
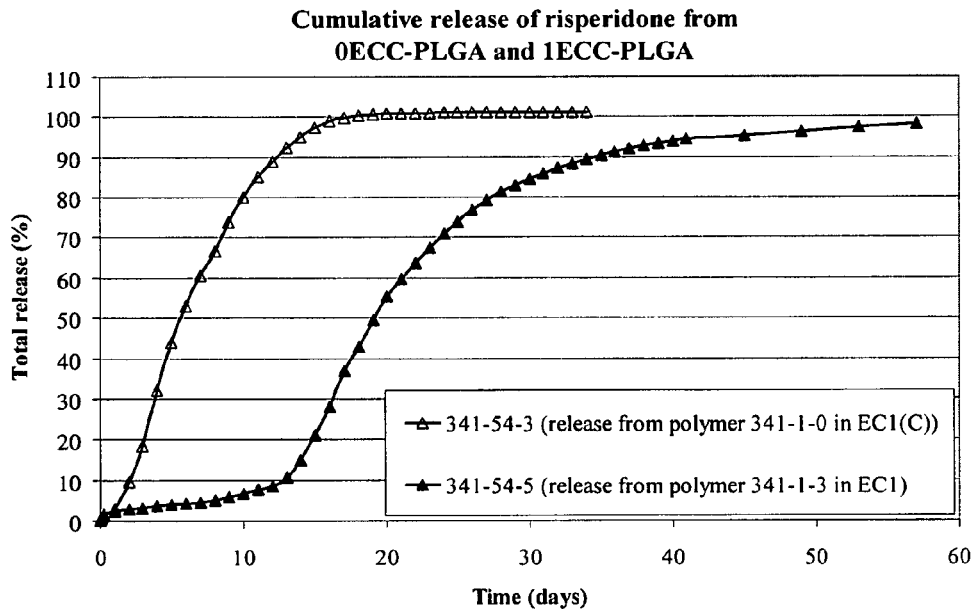

The term "pharmaceutical formulation" is used herein to mean a composition which (i) is suitable for administration to a human being or other mammal or which can be treated, e.g. sterilized, to make it suitable for such administration, and (ii) comprises at least one drug and at least one ECC polymer. The formulation can be part or all of any device that can deliver a drug, including pills, capsules, gels, depots, medical implantable devices (e.g., stents, including self-expanding stents, balloon-expandable stents, drug-eluting stents and stent-grafts, grafts (e.g., aortic grafts), artificial heart valves, cerebrospinal fluid shunts, pacemaker electrodes, endocardial leads, bioerodable implants and the like, and externally manipulated devices (e.g. drug devices and catheters, including catheters which can release a drug, e.g. as a result of heating the tip of the catheter). The pharmaceutical formulation may also include one or more other additives, for example pharmaceutically acceptable excipients, carriers, penetration enhancers, stabilizers, buffers or other materials physically associated with the drug and/or the CYSC polymer to enhance the deliverability of the dosage form and/or the effectiveness of the drug. The formulation may be, for example, a liquid, a suspension, a solid such as a tablet, pill, capsule (including a microcapsule), emulsion, micelle, ointment, gel, emulsion, depot (including a subcutaneously implanted depot), or coating on an implanted device, e.g. a stent or the like. The formulation can for example be applied externally, e.g. as a patch, or a device applied partly externally and partly implanted, or completely implanted or injected subcutaneously.

The term "drug" means a material which is biologically active in a human being or other mammal, locally and/or systemically. Examples of drugs are disclosed in the Merck Index, the Physicians Desk Reference, and in column 11, line 16, to column 12, line 58, of U.S. Pat. No. 6,297,337, and in paragraph 0045 of U.S. 2003/0224974, the entire disclosures of which are incorporated by reference herein for all purposes. Drugs can for example be substances used for the treatment, prevention, diagnosis, cure or mitigation of a disease or illness, including vitamins and mineral supplements; substances which affect the structure or the function of a mammal; pro-drugs, which are substances which become biologically active or more active after they have been placed in a physiological environment; and metabolites of drugs. Examples of drugs are proteins, peptides, small molecule drugs, and antipsychotic drugs. Examples of diagnostic agents are imaging agents containing radioisotopes, contrasting agents containing for example iodine, enzymes, fluorescent substances and the like.

The term "therapeutically effective amount" means an amount of a drug effective to facilitate a desired therapeutic effect.

As an indicator of the rate at which a drug will be released from a pharmaceutical formulation in vivo, it is possible to make use of in vitro tests which are designed to mimic the expected physiological conditions in the delivery site or organ of interest (e.g. gastrointestinally for a pill or subcutaneously for an implant). The Examples below make use of such an in vitro test. The results of a suitable in vitro test are no more than an indicator of in vivo results, but are useful for making comparative measurements. The terms "association", "associated" and the like mean any type of interaction, including chemical bonds (including, for example, covalent, ionic and hydrogen bonds) and/or Van der Waals forces, and/or polar and non-polar interaction through other physical constraints provided by molecular structure, and interactions through physical mixing.

In this specification, parts, ratios and percentages are by weight, except where otherwise noted. Temperatures are in degrees Centigrade (° C.). Molecular weights of polymers are in Daltons, are number average molecular weights (Mn) unless stated to be weight average molecular weights (Mw), and are measured by gel permeation chromatography (GPC) with a light scattering detection method, for example using a DAWN DSP laser photometer from Wyatt Technology. In defining the polymers, this specification uses the terms "melting point" (often abbreviated to Tp), "onset of melting temperature" (often abbreviated to To) and "heat of fusion" (which is a measure of crystallinity of the polymer, is expressed in J/g and is often abbreviated to $\Delta H$). Tp, To and $\Delta H$ are determined using a differential scanning calorimeter (hereinafter DSC), e.g. a Q 100 DSC from TA Instruments at a rate of temperature change of 10° C./min, e.g. from −10 to 150° C. Tp is the peak melting temperature, and To is the temperature at the intersection of the baseline of the DSC peak and the onset line, the onset line being defined as the tangent to the steepest part of the DSC curve below Tp. Unless otherwise stated, the values of Tp, To and $\Delta H$ are measured on the second heat cycle.

General Representations Concerning the Disclosure.

In this specification, reference is made to particular features of the invention (including for example components, ingredients, elements, devices, apparatus, systems, groups, ranges, method steps, test results, etc). It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally.

As used in this specification, the singular forms "a", "an", and "the" include plural reference unless the context clearly dictates otherwise. Thus, for example, a reference to "a part" includes a plurality of such parts.

The term "comprises" and grammatical equivalents thereof are used in this specification to mean that, in addition to the features specifically identified, other features are optionally present. For example a formulation which comprises an ECC polymer and a drug can contain a single ECC polymer and a single drug, or two or more ECC polymers and/or two or more drugs, and optionally contains one or more other ingredients which are not ECC polymers, for example other ingredients as disclosed herein. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number. For example, "from 8 to 20 carbon atoms" or "8-20 carbon atoms" means a range whose lower limit is 8 carbon atoms, and whose upper limit is 20 carbon atoms. The terms "plural", "multiple", "plurality" and "multiplicity" are used herein to denote two or more than two features.

Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features (except where the context excludes that possibility). Where reference is made herein to two or more features, this includes the possibility that the two or more features are replaced by a lesser number or greater number of features providing the same function (except where the context excludes that possibility). The numbers given herein should be construed with the latitude appropriate to their context and expression; for example, each number is subject to variation which depends on the accuracy with which it can be measured by methods conventionally used by those skilled in the art.

b Moieties b is a bond or a divalent moiety. For example, b may be (i) a covalent bond (as for example when the carboxyl group at the end of a PLGA is esterified by an alcohol containing a Cy moiety) or (ii) a divalent organic moiety, for example (a) a carboxyl group (as for example when the hydroxyl group at the end of a PLGA is esterified by a carboxylic acid comprising a Cy moiety) or (b) an aliphatic, aromatic or mixed aliphatic/aromatic moiety, for example the residue of a polyol resulting from the esterification of the carboxyl group at the end of a PLGA by a polyol, followed by esterification of one or more of the remaining hydroxyl groups of the polyol by an acid containing a Cy moiety. Other examples of b moieties are moieties comprising for example ester, carbonyl, amide, amine oxide, hydrocarbon (for example phenylene), amino, ether, polyoxyalkylene, or an ionic salt linkage (for example a carboxyalkyl ammonium, sulfonium or phosphonium ion pair).

Cy Moieties

The ECC polymer contains one or more Cy moieties such that the polymer has a heat of fusion of at least 10 J/g and an associated Tp resulting from crystallization of the Cy moieties. Other polymers having crystallinity which results from the presence of Cy moieties are well known and have been referred to as side chain crystalline polymers (sometimes abbreviated to SCC polymers or SCCPs). Patents and other publications relating to SCC polymers include J. Poly. Sci. 60, 19 (1962); J. Poly. Sci, (Polymer Chemistry) 7, 3053 (1969), 9, 1835, 3349, 3351, 3367, 10, 1657, 3347, 18, 2197, 19, 1871; J. Poly. Sci, Poly-Physics Ed 18 2197 (1980); J. Poly. Sci, Macromol. Rev, 8, 117 (1974); Macromolecules 12, 94 (1979), 13, 12, 15, 18, 2141, 19, 611; JACS 75, 3326 (1953), 76; 6280; Polymer J 17, 991 (1985); and Poly. Sci USSR 21, 241 (1979); U.S. Pat. Nos. 4,830,855, 5,120,349, 5,129,180, 5,156,911, 5,254,354, 5,387,450, 5,412,035, 5,469,867, 5,665,822, 5,752,926, 5,783,302, 6,013,293, 6,060,540, 6,199,318, 6,210,724, 6,224,793, 6,255,367, 6,376,032, 6,492,462, 6,540,984, 6,548,132, 6,831,116, 6,989,417, and 7,101,928; and US Patent Application Publications Nos. 2001/0018484 2002/0090425 and 2002/0127305. The entire disclosure of each of those publications, patents and patent publications is incorporated herein by reference for all purposes.

When the ECC polymer contains more than one b—Cy moiety, all the Cy moieties can be the same, or there can be a plurality of (i.e. two or more) different types of moiety which differ from each other in one or both of b and Cy. Some useful Cy moieties optionally include polyoxyalkylene, e.g. polyoxyethylene, units. Such a polyoxyalkylene unit can be a homopolymer, random copolymer, or block copolymer containing 2 to 100, e.g. 5 to 100, preferably 5 to 60, oxyalkylene units, preferably 2-20, e.g. 2-4, oxyalkylene units.

The repeating units of an ECC polymer can consist essentially of the moieties of the formula (1) and (2), i.e. the polymer is derived from a PGA (in which each of $F^1$ and $F^2$ is hydrogen in each of the repeating units), a PLGA (in which each of $F^1$ and $F^2$ is hydrogen in some of the repeating units, and one of $F^1$ and $F^2$ is hydrogen and the other of $F^1$ and $F^2$ is methyl in the other repeating units) or a PLA (in which one of F1 and F2 is methyl and the other of F1 and F2 is hydrogen in each of the repeating units). Alternatively, the polymer can also contain repeating units of a different type, optionally providing further carboxy linkages in the polymer backbone, for example units derived from caprolactone. A drug associated with an ECC polymer can for example be delivered at a controlled rate and/or at a desired location, the rate and/or the location being influenced for example by a chemical and/or physical condition which modifies the association of the drug and the polymer. The condition can for example be an environment which causes the polymer to undergo a chemical change (for example the weakening or creation of any kind of chemical association, e.g. oxidation, reduction or hydration) and/or a change in physical state (for example the weakening or creation of any kind of physical association), e.g. a change in viscosity resulting from melting or crystallization, for example caused by internal or external heating) including an environment having a particular pH range or the presence of an enzyme.

The following statements disclose optional characteristics of the invention. Two or more of the stated characteristics can be present at the same time, except where the context makes this impossible.

(A) the ECC polymer (A1) has a molecular weight less than 8,000, or less than 7,000, or less than 5,000;

(A2) has a value of (Tp−To) which is less than $Tp^{0.7}$, e.g. less than $Tp^{0.6}$, or less than 10° C.;

(A3) contains less than 30%, e.g. less than 20% or less than 10%, and/or more than 1%, e.g. more than 2% or more than 4%, molar percent of units comprising Cy moieties;

(A4) has a heat of fusion of at least 10, or at least 20 J/g.;

(A5) at least 50 mol percent, e.g. at least 70 mol % or at least 80 mol %, of the repeating units forming the backbone of the polymer are free of Cy moieties;

(A6) the terminal units have one or more of the formulas (2A)-(2C) below

—Cy                                                                (2A)

—O—CO-Cy                                 (2B)

-$R_{pbalc}$—CO-Cy                         (2C)

where $R_{pbalc}$ is the residue of a polyol, for example a polyethylene glycol, 1,3-propanediol, glycerin or sorbitol, and optionally contains one or more Cy moieties, the terminal and other Cy moieties, if any, being introduced for example by esterification, transesterification or alkylation of one or more of the hydroxyl groups, e.g. by reaction with an acid or acid chloride containing a Cy moiety; and has for example the formula —$CH_2$—CH(OH)—$CH_2$—O—CO-Cy or —$CH_2$—CH(O—CO-Cy)-$CH_2$—O—CO-Cy;

(A7) the polymer contains less than 170 repeating units of formula

—$CF^1F^2$—CO—;

(A8) the polymer is prepared by a process which comprises copolymerizing one or more monomers, i.e. one or more of lactic acid and glycolic acid, and their cyclic dimers, lactide and glycolide, which will result in the repeating units of formula (1) and one or more monomers or components which will result in the terminal units which have formula (2) or which can be converted into terminal units of formula (2). For example, (i) an alcohol containing a Cy moiety can be reacted with lactic acid and glycolic acid, or (ii) a polyol, for example glycerine, 1,3-propanediol or 1,6-hexanediol, can be reacted with glycolic acid and lactic acid to form a PLGA glyceride ester which is end capped with an excess of a carboxylic acid containing a Cy moiety, for example stearic acid or behenic acid; (A9) the polymer is prepared by endcapping a preformed polymer having the formula HO—(—$CF^1F^2$—CO—O—)$_n$—H where n is an integer less than 170; the preformed polymer, if prepared by the polymerization of lactide and glycolide, will consist predominantly of pairs of identical repeating units, and if prepared by the polymerization of the monomers (lactic and glycolic acids) will have randomly distributed repeating units; for example (A9a) the polymer is prepared by a process which includes the step of reacting the terminal hydroxyl group of a preformed PLA, PLGA or PGA polymer with a monomer or component, e.g. a carboxylic acid or acid chloride which contains a Cy moiety, or with a monomer or component which contains a moiety which can be further reacted so that it comprises a Cy moiety; or (A9b) the polymer is prepared by a process which includes the step of reacting the terminal carboxyl group of a preformed PLA, PLGA or PGA polymer with a component, e.g. an alcohol, which contains a Cy moiety, or with a component which contains a moiety which can be further reacted, e.g. by transesterification, so that it comprises a Cy moiety. For example, the preformed polymer can be reacted with (i) an alcohol containing a Cy moiety, or (ii) a polyol, for example glycerine, 1,3-propanediol or hexanediol, followed by reaction of one or more of the remaining hydroxyl groups of the polyol with an excess of a carboxylic acid containing a Cy moiety, for example stearic acid or behenic acid; or (A9c) the polymer is prepared by a process which includes the step of reacting the terminal hydroxyl group of a preformed PLA, PLGA or PGA polymer with a dicarboxylic acid or anhydride, e.g. succinic anhydride or succinic acid (succinylation); the resulting product, which may have a relatively high molecular weight in which case it may be in the form of a gel, facilitates formulation mixing in-situ, and/or may enable easy mixing of a protein or peptide drug at one pH and release at another pH; or (A9d) a preformed PLA, PLGA or PGA polymer is reacted with methacrylic anhydride and this reaction mixture is copolymerized with an ethylenically unsaturated monomer containing a Cy moiety; or (A10) contains at least 10%, e.g. 10-40%, by weight of the Cy units.

(B) the formulation (B1) contains one or more other polymers physically mixed with the ECC polymer. Examples of such other polymers include conventional SCC polymers, main chain crystalline polymers, and bioerodable polyesters. Specific examples of such other polymers include poly (epsilon-caprolactone (PCL), poly(dioxanone), polyhydroxybutyrate (PHB), polyhydroxyvalerate (PHV), polyhydroxyalkanoates (PHAs), polyesters from 3-hydroxypropionic acid, polymers derived from methylene carbonate, polyanhydrides, polyorthoesters, naturally occurring polymers or their hydrolysis or degraded products such as sugars, hydrolyzed starches, hyaluronan (also called hyaluronic acid or hyaluronate), chitan, chitosan, and alkyl polylactides including those disclosed in WO 2007/0142461 (Baker et al.), U.S. Pat. No. 6,469,133, US published application Nos. 20070142461 and 20010044514; or (B 2) includes other components which are not drugs, e.g. pharmaceutical excipients, fillers, carrier materials etc. which modify or improve the drug release, improve its physical and/or chemical stability, dosage form performance, processing, manufacturing, etc., including UV absorbers, fragrances, antioxidants, preservatives and disinfectants.

In some embodiments of the invention, the drug and the polymer are such that, when they are formulated into a release sample in the form of a thin flat disc by the procedure described in the Examples below and tested by each of the two release tests described in the Examples below, the drug is released, in at least one of the two tests, (a) at a substantially constant rate over a period of at least 10 days in the first 20 days, and in a total amount less than 30%, e.g. less than 20%, over the first 20 days, and/or (b) in a total amount less than 30%, preferably less than 20%, over the first 10 days, preferably over the first 20 days, particularly over the first 30 days, and/or (c) at a substantially constant rate over the first 10 days, preferably over the first 20 days, and in a total amount less than 20%, e.g. less than 10%, over the first 10 days, preferably over the first 20 days.

In some embodiments of the invention, the formulation, when tested by a release test in which the formulation is exposed to a buffer solution which is maintained at a pH of 5.5, for example a buffer solution as used in the release test for risperidone samples described in the Examples below, releases the drug (a) at a substantially constant rate over a period of at least 10 days in the first 20 days, and in a total amount less than 30%, e.g. less than 20%, over the first 20 days, and/or (b) in a total amount less than 30%, preferably less than 20%, over the first 10 days, preferably over the first 20 days, particularly over the first 30 days, and/or (c) at a substantially constant rate over the first 10 days, preferably over the first 20 days, and in a total amount less than 20%, e.g. less than 10%, over the first 10 days, preferably over the first 20 days.

In some embodiments of the invention, the formulation, when tested by a release test in which the formulation is exposed to a buffer solution which is maintained at a pH of 7.4, for example a buffer solution as used in the release test for diclofenac sodium samples described in the Examples below, releases the drug (a) at a substantially constant rate over a period of at least 10 days in the first 20 days, and in a total amount less than 30%, e.g. less than 20%, over the first 20 days, and/or (b) in a total amount less than 30%, preferably less than 20%, over the first 10 days, preferably over the first 20 days, particularly over the first 30 days.

EXAMPLES

The invention is illustrated by the following Examples. The Examples illustrating the preparation of the ECC polymers are summarized in Table EC1 below. Table EC1 identifies the ingredients used, and the amounts thereof in grams, and the molecular weight and DSC values of various products. In the PLGA polymers used in the Examples, the molar ratio of (units derived from) glycolic acid to lactic acid was 1:1. After the Table, there is a detailed account of the procedures used in each of the Examples. The heading of each detailed example includes an abbreviation indicating the polymer produced in the example, in the form PLGA, indicating that the polymer is an unmodified PLGA [in comparative Example EC1(C)], or nECC-PLGA, where n is 1, 2, 3 or 4, indicating that the polymer is an end-capped PLGA containing 1, 2, 3 or 4 Cy moieties.

TABLE EC1

| Example No. | EC1 341-1-3 | EC1(C) 341-1-0 | EC2 338-80 | EC3 341-41-5R | EC4 338-55 | EC5 338-56 | EC6(a) 338-75 | EC6(b) 338-77 |
|---|---|---|---|---|---|---|---|---|
| Glycolic acid | 51.925 | 57.011 | — | 55.53 | — | — | — | — |
| Lactic acid 85% + solution | 70.291 | 77.175 | — | 75.18 | — | — | — | — |
| C6 PLGA | | | | | 5.034 | — | — | |
| C22 alcohol | 11.15 | — | — | — | — | — | — | |
| C22 acid | — | — | — | 5.53 | 1.145 | 2.071 | — | 1.272 |
| EC1 | — | — | 16.055 | — | — | 5.033 | — | |
| Succinic anhydride | — | — | 2.002 | — | — | — | — | |
| EC2 | — | — | — | — | — | — | 6.73 | |
| Glycerol | — | — | — | — | — | — | 60 mL | |
| EC6(a) | — | — | — | — | — | — | | 1.27 |
| To | | | 50.55 Tg16.2 | | 45.95 | 54.77 | | 52.11 |
| Tp | 58 | Tg 18.7 | 57.06 Tg19.2 | 59.8 | 54.17 | 59.89 | | 58.46 |
| Mn | 812 | 1165 | 633 | 665 | 4986 | 3912 | | 6091 |
| Mw | 981 | 1484 | 879 | 1184 | 7080 | 7119 | | 14,235 |

| Example No. | EC7(a) 338-91 | EC7(b) 338-93 | EC8 338-92 | EC9(a) 338-85 | EC9(b) 338-87 | EC9(c) 338-88 | EC10(a) 338-83 | EC10(b) 338-84 |
|---|---|---|---|---|---|---|---|---|
| C22 acid | | 2.044 | | | | 2.504 | | 1.583 |
| Succinic anhydride | | | | 1.465 | | | | |
| EC1 © | | | | 15.027 | | | | |
| EC2 | | | | | | | 7.049 | |
| Glycerol | 35 mL | | 0.282 | | 25 mL | | 30 mL | |
| EC3 | 15.077 | | 8.133 | | | | | |
| EC7(a) | | 3.16 | | | | | | |
| EC9(a) | | | | | 9.85 | | | |
| EC9(b) | | | | | | 2.2 | | |
| EC10(a) | | | | | | | | 1.86 |
| To | | 56.69 | 25.37(1) | | | 51.34 | | 51.54 |
| | | | Tg 9.96 | 44.48(2) | | | | |
| Tp | | 60.35 | 30.72(1) | | | 57.16 | | 57.15 |

TABLE EC1-continued

|    | Tg | 49.29(2) | | |
|----|------|------|------|------|
|    | 18.97 | | | |
| Mn | 4774 | 2479 | 45,370 | 6893 |
| Mw | 18,385 | 3373 | 160,900 | 15,545 |

Example EC1

1ECC-PLGA

Glycolic acid (51.925 g), lactic acid solution (70.291 g) and behenyl alcohol (11.15 g) were weighed into a 1000 ml reaction vessel equipped with a mechanical stirrer and heated to 140° C. After stirring for 15 to 25 min, vacuum was applied to remove water. The reaction was continued under reduced pressure at 140° C. for at least 16 hrs. A clear pale yellow viscous liquid was removed from the vessel while it was still hot. After cooling to room temperature, 85 gram of opaque solid (341-1-3) was obtained.

Example EC1(C)

PLGA

The procedure of Example EC1 was followed, but using glycolic acid (57.011 g) and lactic acid solution (77.175 g) as the starting materials. 84 g of clear solid (341-1-0) was obtained.

Example EC2

1ECC-PLGA

PLGA (16.055 g of polymer 341-1-3, the product of Example EC1), succinic anhydride (2.002 g) and a catalytic amount of p-toluenesulfonic acid were combined with 200 mL toluene in a 250 mL round bottom flask fitted with a condenser and Dean-Stark trap. The reaction was stirred under reflux with a magnetic stir bar under nitrogen in a 135° C. oil bath overnight. The temperature was increased to 150° C. and stirring continued for 2 days, after which toluene was removed by distillation over 4.5 hours. Reaction progress was monitored by FTIR through loss of anhydride peaks at 1864 cm-1 and 1782 cm-1, loss of broad PLGA alcohol peak from 3600-3400 cm-1, and increase in broad acid OH peak from 3300-2400 cm-1. The product was purified by first dissolving in 50 mL warm dichloromethane and adding 50 mL water. The layers were separated in a separatory funnel and the water layer was extracted 1× with 25 mL dichloromethane. The organic layers were combined and washed 3× with 25 mL water. The dicholomethane layer was dried over anhydrous magnesium sulfate which was removed by gravity filtration. The resulting filtrate was condensed under reduced pressure to give 16.3 g product (338-80).

Example EC3

1ECC-PLGA

Glycolic acid (55.53 g), lactic acid solution (75.18 g) and behenic acid (5.53 g) were weighed into a 1000 ml reaction vessel equipped with a mechanical stirrer and heated to 140° C. After stirring for 15 to 25 min, vacuum was applied to remove water. The reaction was continued under reduced pressure at 140° C. for at least 16 hrs. A clear pale yellow viscous liquid was removed from the vessel while still hot. After cooling to room temperature, 90 gram of opaque solid (341-41-5R) was obtained.

Example EC4

2ECC-PLGA

PLGA (5.034 g of polymer Mn 3127 from Durect, Pelham, Ala.), behenic acid (1.145 g) and a catalytic amount of p-toluenesulfonic acid were combined in a 100 mL round bottom flask with 30 mL toluene. The reaction was stirred with a magnetic stir bar under nitrogen and heated for 1 hour until all solids dissolved and the toluene was refluxing. Toluene was removed under reduced pressure over 4 hours followed by continued heating under nitrogen at 140° C. for 3.5 days until completely reacted. Reaction progress was monitored by FTIR through loss of the 1708 cm-1 carboxylic acid carbonyl peak and conversion to an ester carbonyl peak at about 1757 cm-1 (overlap with PLGA ester carbonyl at same shift), and loss of the broad acid OH peak from 3300-2400 cm-1. The product was purified by first dissolving in 35 mL of warm dichloromethane followed by cooling for 5-10 minutes on dry ice until visibly cloudy with a white precipitate. Gravity filtration over fluted filter paper was performed to remove a white solid. Solvent was removed from the solution under reduced pressure yielding 4.3 grams of product (338-55).

Example EC5

2ECC-PLGA

The product of Example EC1 (341-1-3) (5.033 g), behenic acid (2.071 g) and a catalytic amount of p-toluenesulfonic acid were placed in a 250 mL round bottom flask with 50 mL toluene. The reaction was stirred with a magnetic stir bar under nitrogen in a 140° C. oil bath for a quarter hour until all solids dissolved. Toluene was removed under reduced pressure over 2.5 hours followed by continued heating under nitrogen at 140° C. for 3.5 days until completely reacted. Reaction progress was monitored by FTIR as in Example EC4. Any residual toluene was removed under reduced pressure for 1 hour. The product was purified by first dissolving in 40 mL of warm dichloromethane followed by cooling for 5-10 minutes on dry ice until cloudy with white precipitate. Gravity filtration over fluted filter paper was performed to remove a white solid. Solvent was removed from the solution under reduced pressure yielding 3.5 grams of product (338-56).

Example EC6

3ECC-PLGA (a) A carboxy-terminated and C22 terminated PLGA polymer made by the same process as Example EC2 (6.73 g) and 60 mL glycerol were combined in a 250 mL round bottom flask. The reaction was stirred with a magnetic stir bar under nitrogen in a 130° C. oil bath overnight, until reacted. Reaction progress was monitored by taking small samples of the reaction mixture and extracting with dichloromethane, and monitoring by FTIR through the loss of the broad acid OH peak between 3200-2400 cm-1 and the appearance of the glycerol alcohol peak from 3600-3100 cm-1. The product was purified by addition of 100 mL dichloromethane and 100 mL water, stirred and shaken vigorously, and added to a separatory funnel. The resulting layers were separated, and the water layer extracted 3× with 50 mL dichloromethane. The organic layers were combined and washed 3× with 20 mL water, and then dried over anhydrous magnesium sulfate, which was subsequently removed by gravity filtration through fluted filter paper. This extraction and washing process was repeated on the water layers a second time to remove any remaining product, with all resulting organic layers combined and solvent removed under reduced pressure to yield 1.27 grams of intermediate product (338-75).

(b) The 1.27 grams of intermediate product was combined with behenic acid (1.272 g), a catalytic amount of p-toluenesulfonic acid and 200 mL toluene in a 250 mL round bottom flask and fitted with a condenser and collecting funnel. The reaction was stirred under reflux with a magnetic stir bar under nitrogen in a 130° C. oil bath overnight. The temperature was then increased to 135° C. and stirred under reflux for 24 hours until complete. Reaction progress was monitored by the loss of the broad glycerol OH peak from 3600-3100 cm-1, the disappearance of the broad acid OH stretch from 3200-2400 cm-1, and the loss of the behenic acid carbonyl peak at 1706 cm-1 and conversion to ester carbonyl peak at about 1754 cm-1 (overlap with PLGA ester carbonyl peaks). The product was purified by dissolving in warm dichloromethane and cooled over dry ice for 5-10 minutes until white precipitate was formed, which was removed by gravity filtration through fluted filter paper. The filtrate was condensed under reduced pressure to produce 1.93 g of product (338-77).

Example EC7

3ECC-PLGA (a) Acid capped C22 PLGA (15.077 g, the product of Example EC3, 341-41-5R), 35 mL glycerol and a catalytic amount of p-toluenesulfonic acid were combined in a 100 mL round bottom flask. The reaction was stirred by magnetic stir bar under nitrogen and heated in a 130° C. oil bath overnight until reaction was complete. Reaction progress was monitored by taking small samples of reaction mixture and performing a mini-extraction with dichloromethane, with progress monitored through FTIR through the loss of broad acid OH peak from 3300-2300 cm-1 and appearance of broad glycerol OH peak from 3700-3100 cm-1 in product. For purification 50 mL water and 20 mL dichloromethane was added to the reaction flask, warmed, and stirred vigorously until all was dissolved. Using a separatory funnel, the organic layer was isolated and the water layer extracted 2× with 30 mL dichloromethane. The organic layers were then combined and washed 3× with 20 mL water, then dried over anhydrous magnesium sulfate which was then removed by gravity filtration through fluted filter paper. Solvent was removed under reduced pressure to give 3.42 g reaction intermediate (338-91).

(b) 3.16 g of the reaction intermediate, 2.044 g behenic acid, 65 mL toluene, and a catalytic amount of p-toluenesulfonic acid were combined in a 100 mL round bottom flask fitted with condenser and Dean-Stark trap. The reaction was stirred by magnetic stir bar under nitrogen and placed in a 135° C. oil bath, and allowed to reflux for 4.5 days until reaction was complete and yielded approximately 4 grams of product (338-93). Reaction progress was monitored by FTIR through the loss of broad glycerol OH peak from 3700-3100 cm-1, loss of broad behenic acid OH peak from 2800-2300 cm-1, and loss of behenic acid carbonyl peak at 1707 cm-1 and strengthening of 1750 cm-1 ester peak due to acid conversion to ester bond.

Example EC8

3ECC-PLGA

C22 acid capped PLGA (8.133 g, the product of Example EC3, 341-41-5R), glycerol (0.282 g) and a catalytic amount of p-toluenesulfonic acid were combined in a 3 neck 250 ml round bottom flask. The reaction was stirred by magnetic stir bar and heated under nitrogen in a 135° C. oil bath. The reaction was stirred for 1.5 days until reaction was complete and removed from heat to produce the final product (338-92). Reaction progress was monitored by FTIR through the loss of the broad acid OH peak especially from 2800-2400 cm-1, the loss of the glycerol OH peak from 3700-3100 cm-1, and the slight shift of acid carbonyl peak from 1749 cm-1 to 1753 cm-1 due to ester formation (overlap with PLGA ester carbonyl peaks).

Example EC9

4ECC-PLGA (a) PLGA (15.027 g, the product of Example EC1(C), 341-1-0) and succinic anhydride (1.465 g) were combined with 150 mL toluene in a 250 mL round bottom flask fitted with a condenser and Dean-Stark trap. The reaction was stirred by magnetic stir bar under nitrogen in a 135° C. oil bath while refluxing. The reaction was stirred for 3 days until fully reacted. Reaction progress was monitored by FTIR through the loss of succinic anhydride peaks at 1864 cm-1 and 1782 cm-1 and loss of PLGA OH peaks from 3700-3300 cm-1. For purification about 50 mL warm dichloromethane and about 50 mL water were added to the reaction flask and stirred vigorously. The layers were then separated by separatory funnel, with the water layer extracted 2 times each with 30 mL with dichloromethane. The dichloromethane layers were combined and then washed with about 30 mL of water once only. The resulting organic layers were dried over anhydrous magnesium sulfate that was subsequently removed by gravity filtration through fluted filter paper. Solvent was removed under reduced pressure to yield 15.08 g of Intermediate 1 (338-85).

(b) 9.85 g of Intermediate 1 and 25 mL glycerol (large excess) were combined in a 250 mL round bottom flask. The reaction was stirred by magnetic stir bar under nitrogen in a 130° C. oil bath for 20 hours until complete. Reaction progress was monitored by FTIR through loss of the broad acid OH peak between 3200-2500 cm-1 and the appearance of the glycerol alcohol peak from 3700-3200 cm-1. The reaction was purified by adding ~50 mL warm dichloromethane and ~50 mL water to the flask and stirring vigorously. The layers were then separated in a separatory funnel, and the water layer extracted 2 times each with 50 mL dichloromethane. All organic layers were combined and washed 3 times each with ~40 mL of water. The organic layer was then dried over anhydrous magnesium sulfate, which was then removed from gravity filtration through fluted filter paper. Solvent was removed under reduced pressure to give 2.41 g of Intermediate 2 (338-87).

(c) 2.2 g of Intermediate 2, 2.504 g behenic acid and a catalytic amount of p-toluenesulfonic acid were combined in a 250 mL round bottom flask with 150 mL toluene. The reaction was stirred with a magnetic stir bar under nitrogen and stirred in a 135° C. oil bath under reflux, while fitted with a condenser and Dean-Stark trap. The reaction was stirred overnight, at which point solvent was drained the flask placed under reduced pressure to remove the remaining toluene. The reaction was then stirred in the 135° C. oil bath under nitrogen for 24 hours until complete and removed from heat. The reaction progress was monitored by FTIR through the loss of the broad glycerol OH peak from 3700-3200 cm-1, the loss of the broad acid OH stretch from 3100-2400 cm-1, and the loss of the behenic acid carbonyl peak at 1703 cm-1 and conversion to ester carbonyl peak at about 1757 cm-1 (overlap with PLGA ester carbonyl peaks). The reaction was purified by dissolving the sample in warm dichloromethane to dissolve and cooled over dry ice for 5-10 minutes until cloudy with white precipitate. Precipitate was removed by gravity filtration through fluted filter paper and the filtrate was condensed under reduced pressure to produce the final product (338-88) with yield of 2.91 g.

Example EC10

3ECC-PLGA

The procedure of Example EC6 was followed, but using the product from Example EC2 (338-80, 7.049 g) and 30 mL of glycerol to obtain intermediate 338-83. The intermediate 338-83 (1.86 g) was reacted with behenic acid (1.583 g) as in Example EC6 until the reaction was complete. After purification, 2.84 g of product (338-84) was obtained.

Examples of the Preparation and Testing of Pharmaceutical Formulations

Mixtures of drug (either risperidone or diclofenac sodium) and polymer were prepared at 9.1% drug loading by mixing the drug with the polymer in chloroform at the ratio of drug/polymer/chloroform=1/10/35 (wt/wt/wt) at 70° C., followed by evaporation of chloroform in a 70° C. oven, and removal of residual chloroform under reduced pressure at 70° C. The drug/polymer mixtures formed a single phase above the Tp of the polymer. Release samples were prepared as a thin flat disc in a 20 ml scintillation vial (28×61 mm=OD×H) by loading 0.5 gram of the prepared polymer/drug mixture into the vial and warming to 50-70° C., allowing the mixture to flow and fuse together. After cooling the mixture to a temperature below Tp, a solid disc with a smooth uniform surface formed at the bottom of the vial backspace.

Release Test for Risperidone Samples

The risperidone samples were tested by covering the polymer/drug disc with 12.6 grams of a buffer solution at pH=5.5 (50 mM ionic strength, 150 mM NaCl and containing 0.01% w/v Tween-20). The buffer solution was removed and replaced by 12.6 grams of fresh buffer solution at scheduled sampling times, e.g. at 1 min, 2 hr, 6 hr, daily, weekly, or as necessary. The amount of risperidone released into the sample solution was measured by UV-Vis against a standard curve established by using the absorption signal at $\lambda$=276.93 nm.

The buffer solution used to test the risperidone/polymer samples was prepared by adding to 100 ml DI water, 0.16 g of monosodium phosphate monohydrate and 1.04 g of disodium phosphate, followed by NaCl and Tween-20 to a final concentration of 0.9% and 0.01% w/v, respectively. The pH was adjusted to 5.5 with 0.1N HCl as necessary.

Release Test for Diclofenac Sodium Samples

The diclofenac sodium samples were tested by covering the polymer/drug with 5 grams of buffer solution with pH=7.4 (50 mM ionic strength, 150 mM NaCl and containing 0.01% w/v Tween-20). The buffer solution was removed and replaced by 5 grams of fresh buffer solution at scheduled sampling times, e.g. at 1 min, 2 hr, 6 hr, daily, weekly, or as necessary. The amount of diclofenac sodium released into the sample solution was measured by UV-Vis against a standard curve established by using the absorption signal at $\lambda$=276.93 nm.

The buffer solution used to test the diclofenac sodium samples was the same as that used to test the risperidone polymer samples, except that its pH was adjusted to 7.4 with 0.1N HCl or 0.1N NaOH as necessary.

FIGURES

Figure 2:
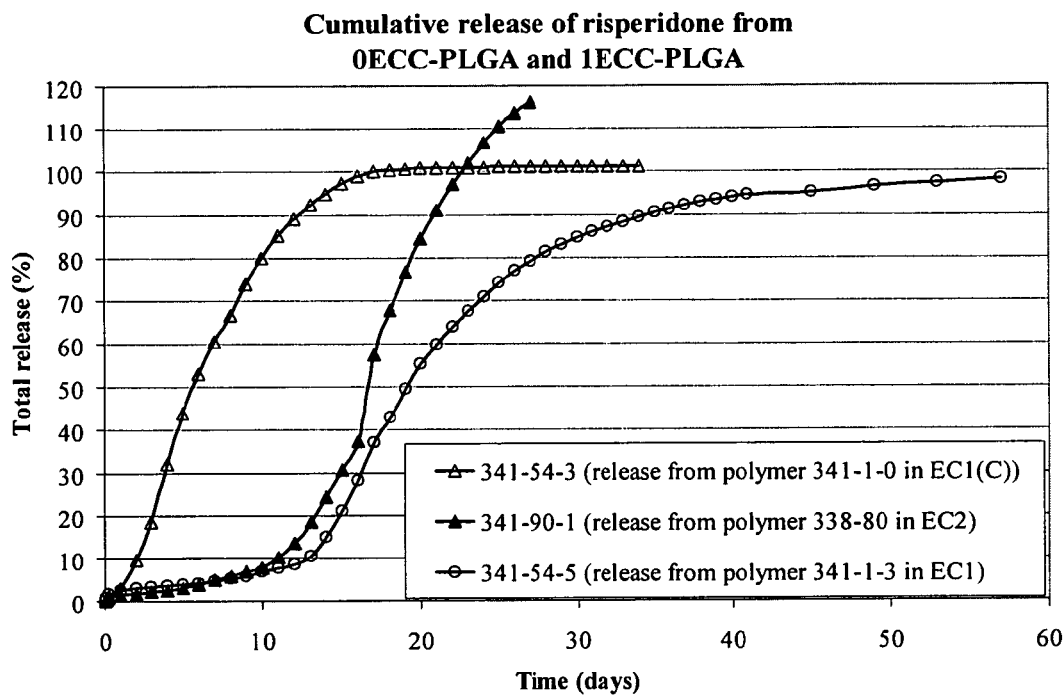
Figure 3:
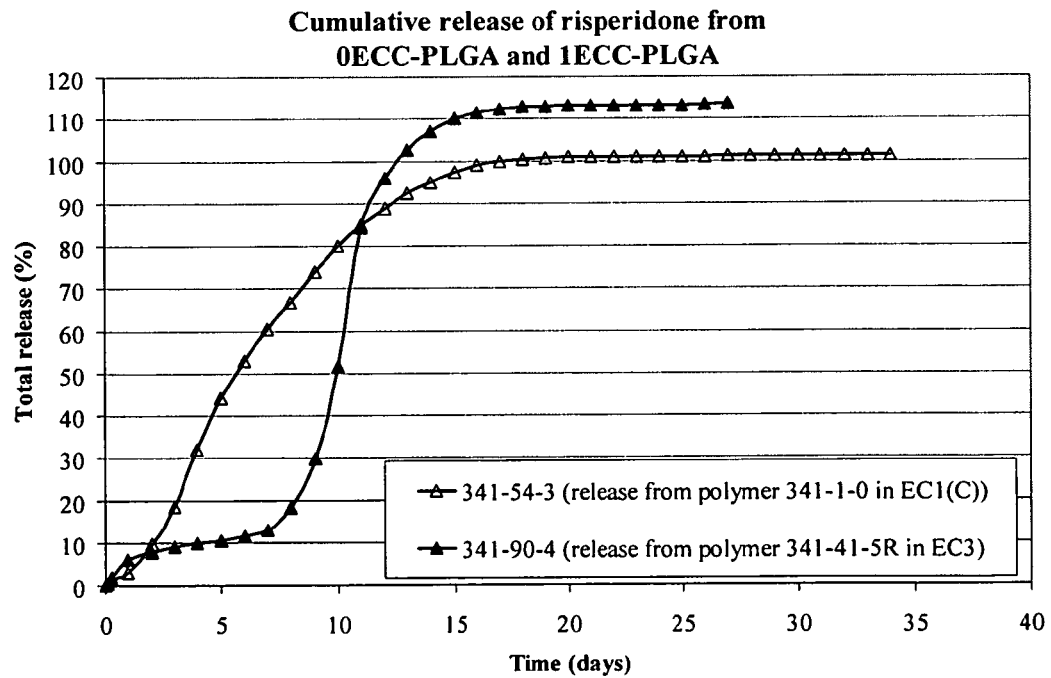
Figure 4A:
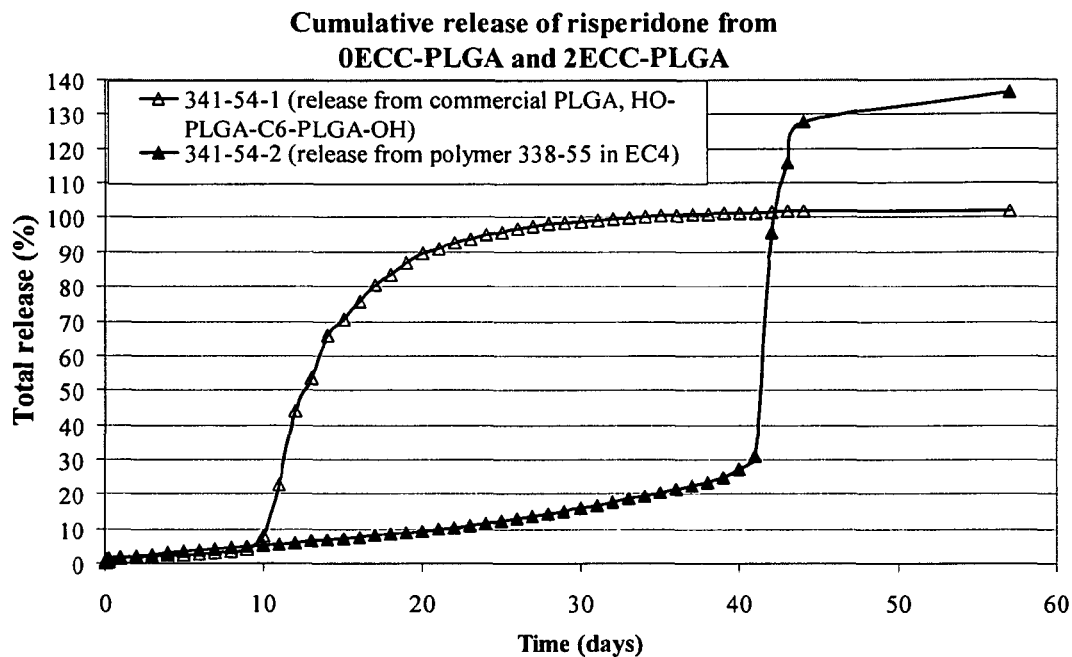
Figure 5A:
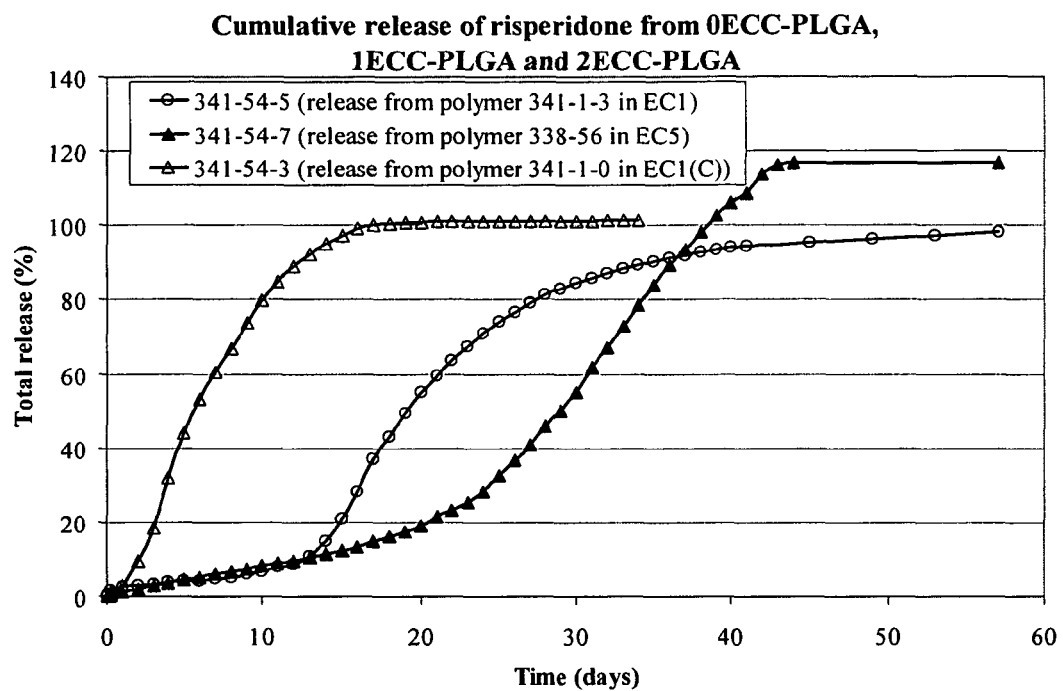
Figure 6:
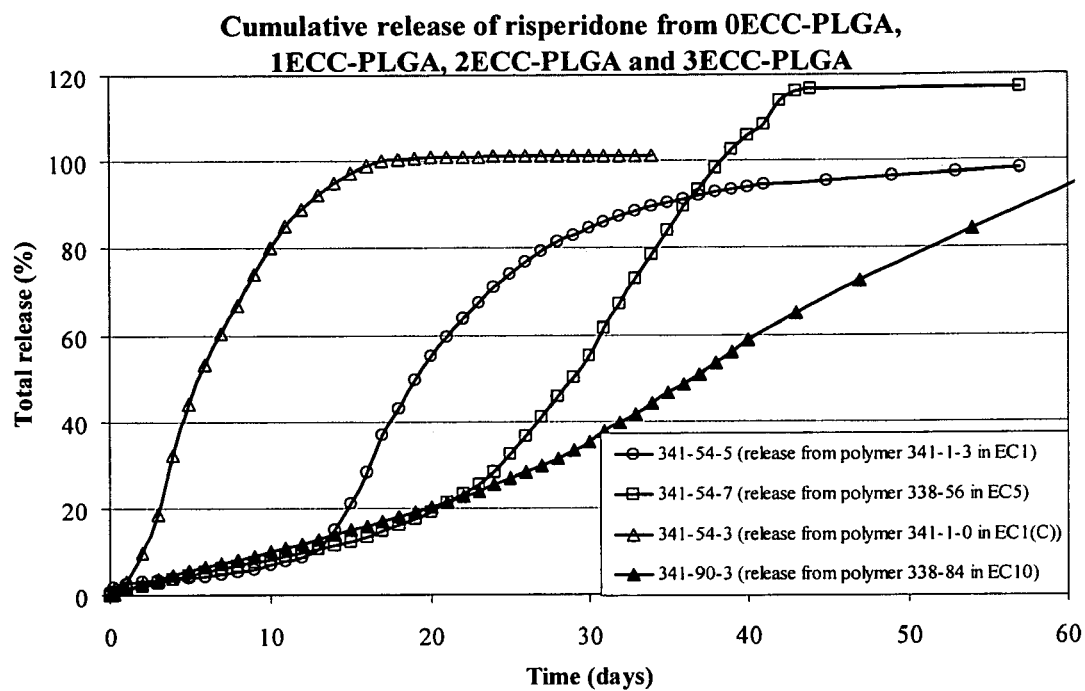
Figure 7:
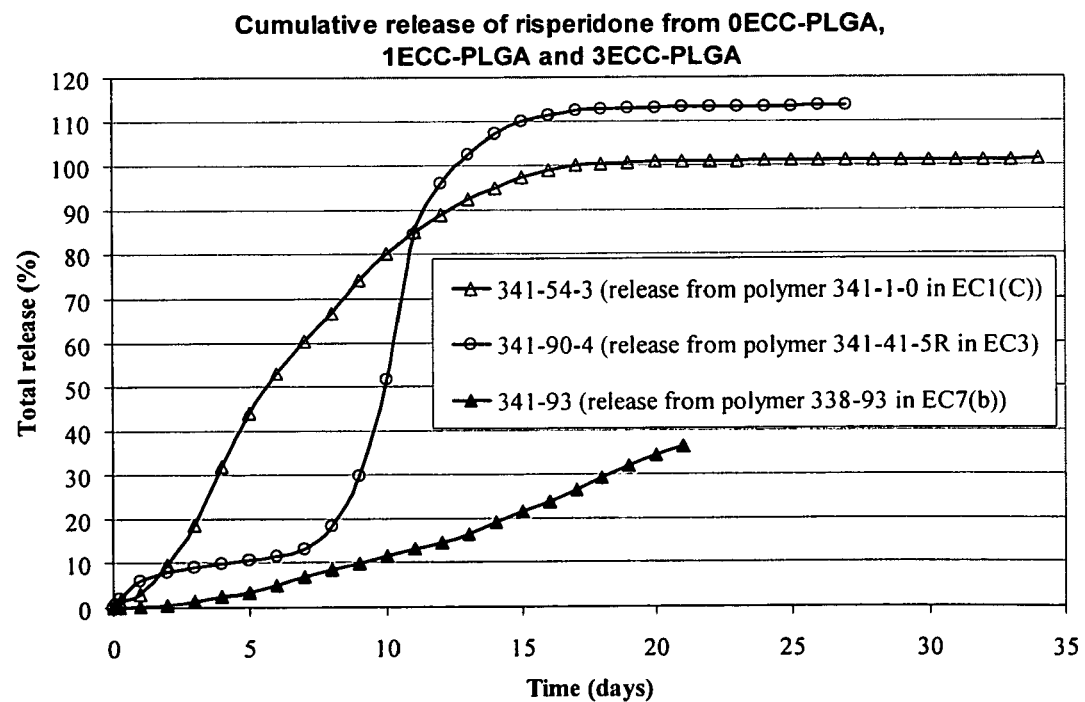
Figure 8:
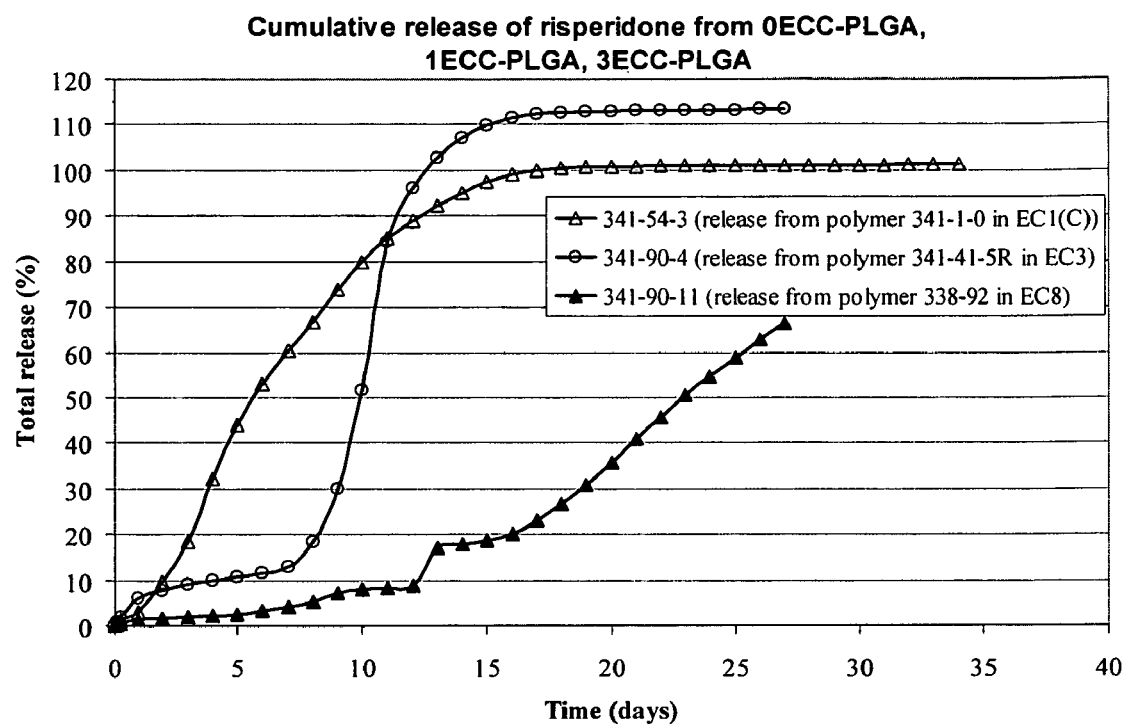

The results of the testing are shown in the accompanying drawings in which FIGS. 1a, 2, 3, 4a, 5a, 6, 7 and 8 show the cumulative release of risperidone from (i) a risperidone-containing mixture based on the unmodified PLGA polymer prepared in Example EC1(C), or, in FIG. 4a, based on a commercially available unmodified PLGA polymer, and from (ii) one or more risperidone-containing mixtures based on one of the ECC polymer prepared in the Examples, namely based on Example EC1 in FIG. 1a, based on Examples EC1 and EC2 in FIG. 2, based on Example EC3 in FIG. 3, based on Example EC4 in FIG. 4a, based on Examples EC1 and EC5 in FIG. 5a, based on Examples EC1, EC5 and EC10 in FIG. 6, based on Examples EC3 and EC7b in FIG. 7, and based on Examples EC3 and EC8 in FIG. 8.

Figure 1B:
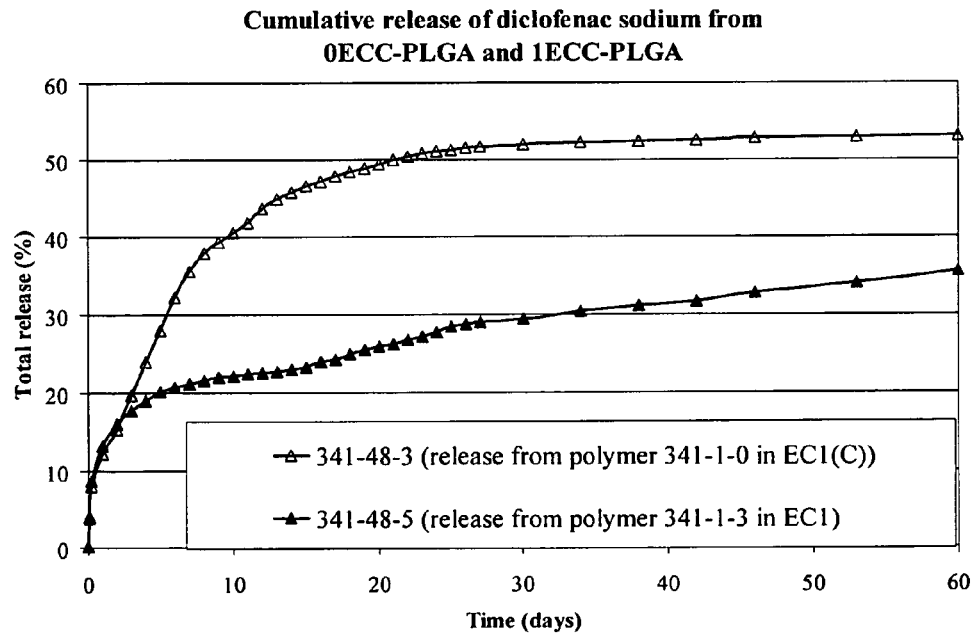
Figure 4B:
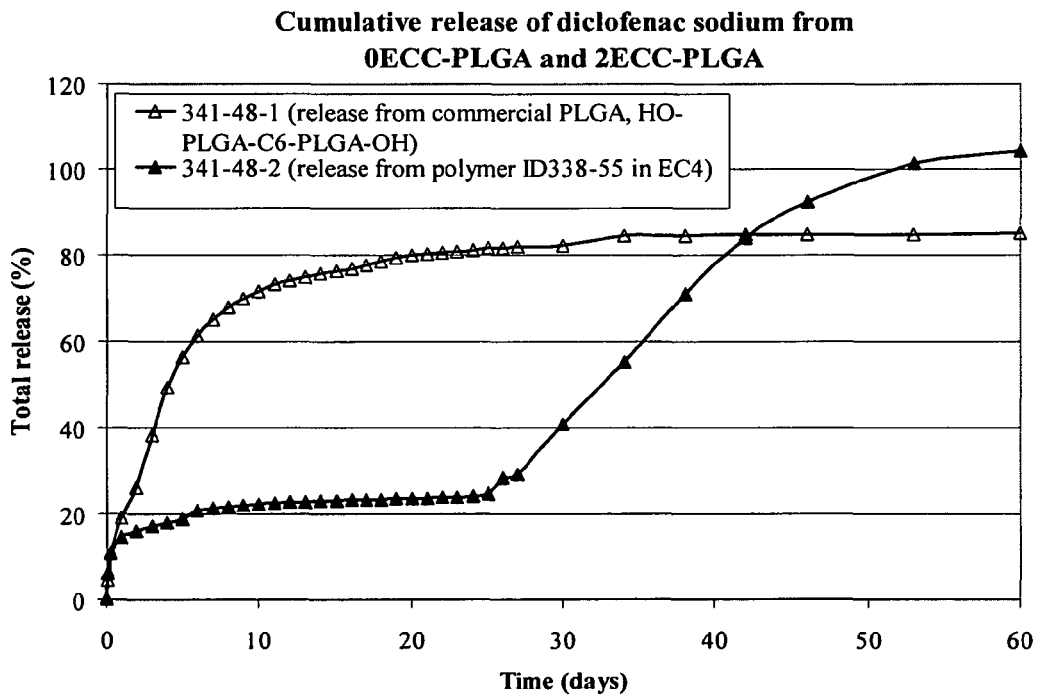
Figure 5B:
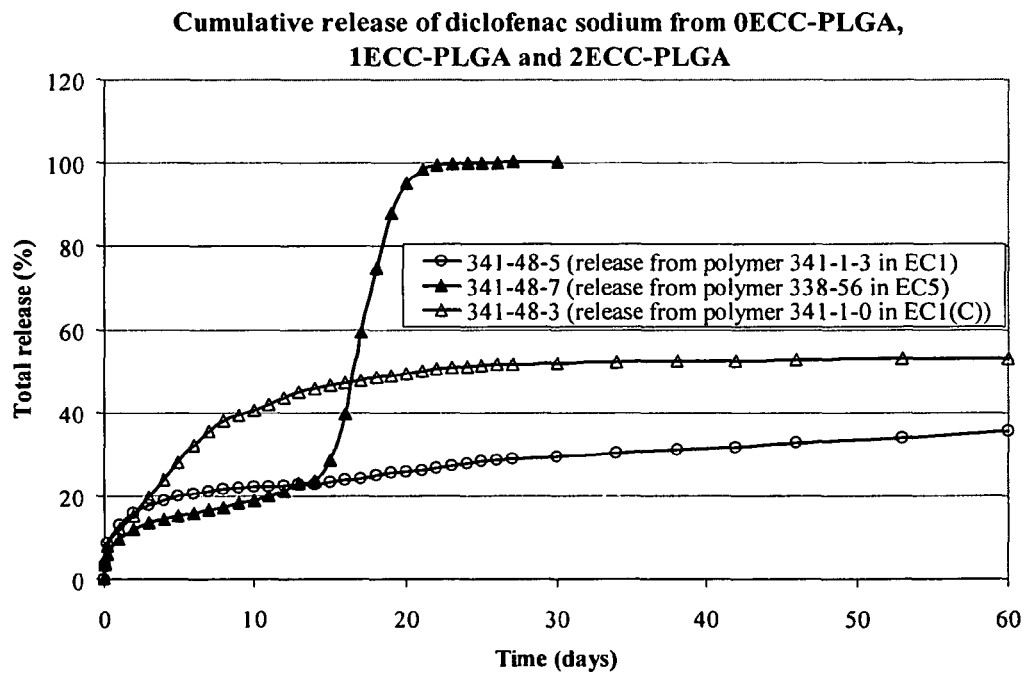

FIGS. 1b, 4b and 5b show the cumulative release of diclofenac sodium from (i) a diclofenac sodium-containing mixture based on the unmodified PLGA polymer prepared in Example EC1(C), or, in FIG. 4b, based on a commercially available unmodified PLGA polymer, and from (ii) one or more diclofenac sodium-containing mixtures based on one of the ECC polymer prepared in the Examples, namely based on Example EC1 in FIG. 1b, based on Example EC4 in FIG. 4b, and based on Examples EC1 and EC5 in FIG. 5b.

The ECC polymers are novel polymers in their own right, and although they are not claimed as such in this application, Applicant intends to claim them as novel polymers in a related application. Furthermore, the ECC polymers can be used in applications other than the delivery of drugs, and applicant intends to claim such uses in one or more related applications. Furthermore, there are other polymers which are similar to ECC polymers, some of which are novel polymers in their own right, and which can be used for the delivery of drugs and in other applications, and those other polymers and their uses will be claimed in one or more related applications. This statement is made for the avoidance of doubt, and to nullify any possible misunderstanding that Applicant is dedicating to the public inventions which are not included within the claims of this application.

We claim:

1. A pharmaceutical formulation comprising a drug and a polymer, wherein
 (1) the polymer comprises a plurality of polymeric molecules each of which consists essentially of
  (i) a polymer backbone which comprises a plurality of repeating units having the formula

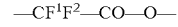  (1)

wherein
 $F^1$ is hydrogen and $F^2$ is hydrogen or methyl, the repeating units being the same or different, and (ii) at least one terminal unit which has the formula -b—Cy    (2)

wherein
Cy consists of an n-alkyl moiety containing 18-24 carbon atoms, and
b is a bond or a moiety which has a valence of at least 2 and which links the Cy moiety to the polymer backbone;
wherein each terminal unit having formula (2) is a moiety selected from the group consisting of
(2A) moieties (i) in which b is a bond, (ii) which have the formula —Cy and (iii) which are directly linked to the terminal —CO—O— moiety of one of the repeating units having formula (1),
(2B) moieties (i) in which b is a moiety having the formula —O—CO—, (ii) which have the formula —O—CO—Cy and (iii) which are directly linked to the terminal —CF$^1$F$^2$—moiety of one of the repeating units having formula (1), and
(2C) moieties (i) in which b is a moiety having the formula
-R$_{pbalc}$—CO—, (ii) which have the formula
-R$_{pbalc}$—CO—Cy, where R$_{pbalc}$ is the residue of a polyol, and (iii) which are directly linked to the terminal —CO—O— moiety of one of the repeating units having formula (1);
(2) the polymer has a crystalline melting temperature, Tp, of at least 40° C., an onset of melting temperature, To, such that the value of (Tp–To) is less than Tp$^{0.7}$, and a heat of fusion of at least 5 J/g, and
(3) the polymer has a number average molecular weight, Mn, of less than 10,000.

2. A formulation according to claim 1 wherein the drug is RISPERIDONE.

3. A formulation according to claim 1 wherein the drug is diclofenac sodium.

4. A formulation according to claim 1 wherein Cy consists of an n-alkyl moiety containing 22 carbon atoms.

5. A formulation according to claim 1 wherein at least some of the polymeric molecules contain at least three Cy moieties, and the polymer has a heat of fusion of at least 10 J/g.

6. A pharmaceutical formulation comprising a drug and a polymer, wherein
(1) the polymer comprises a plurality of polymeric molecules each of which consists essentially of
(i) a polymer backbone which comprises a plurality of repeating units having the formula

—CF$^1$F$^2$—CO—O—    (1)

wherein
F$^1$ is hydrogen and F$^2$ is hydrogen or methyl, the repeating units being the same or different, and
(ii) at least one terminal unit which has the formula -b—Cy    (2)

wherein
Cy consists of an n-alkyl moiety containing 18-24 carbon atoms and a polyoxyalkylene unit, and
b is a bond or a moiety which has a valence of at least 2 and which links the Cy moiety to the polymer backbone;
wherein each terminal unit having formula (2) is a moiety selected from the group consisting of (2A) moieties (i) in which b is a bond, (ii) which have the formula —Cy and (iii) which are directly linked to the terminal —CO—O— moiety of one of the repeating units having formula (1),
(2B) moieties (i) in which b is a moiety having the formula —O—CO—, (ii) which have the formula —O—CO—Cy and (iii) which are directly linked to the terminal —CF$^1$F$^2$—moiety of one of the repeating units having formula (1), and
(2C) moieties (i) in which b is a moiety having the formula
-R$_{pbalc}$—CO—, (ii) which have the formula
-R$_{pubic}$—CO—Cy, where R$_{pbalc}$ is the residue of a polyol, and (iii) which are directly linked to the terminal —CO—O— moiety of one of the repeating units having formula (1);
(2) the polymer has a crystalline melting temperature, Tp, of at least 40° C., an onset of melting temperature, To, such that the value of (Tp–To) is less than Tp$^{0.7}$, and a heat of fusion of at least 5 J/g, and
(3) the polymer has a number average molecular weight, Mn, of less than 10,000.

7. A formulation according claim 1 wherein the formulation, when tested by a release test in which the formulation is exposed to a buffer solution which is maintained at a pH of 5.5, releases the drug according to at least one of paragraphs (a)-(c) below
(a) at a substantially constant rate over a period of at least 10 days in the first days, and in a total amount less than 30%,
(b) in a total amount less than 30% over the first 10 days, and
(c) at a substantially constant rate over the first 10 days, and in a total amount less than 20% over the first 10 days.

8. A formulation according to claim 1 wherein the formulation, when tested by a release test in which the formulation is exposed to a buffer solution which is maintained at a pH of 7.4, releases the drug
(a) at a substantially constant rate over a period of at least 10 days in the first 20 days, and in a total amount less than 30% over the first 20 days, and
(b) in a total amount less than 30%, preferably less than 20%, over the first 10 days, preferably over the first 20 days, particularly over the first 30 days.

9. A pharmaceutical formulation comprising a drug and a polymer, wherein
(1) the polymer consists essentially of a plurality of polymeric molecules each of which consists essentially of
(i) a polymer backbone which consists essentially of a plurality of repeating units having the formula

—CH$_2$—CO—O—    (1A)

and a plurality of repeating units having the formula

—CH(CH$_3$)—CO—O—    (1B)

and
(ii) a plurality of terminal units each of which has the formula

-b—Cy    (2)

wherein
Cy consists of an n-alkyl moiety containing 18-24 carbon atoms, and
b is a bond or a moiety which has a valence of at least 2 and which links the Cy moiety to the polymer backbone;

wherein each terminal unit having formula (2) is a moiety selected from the group consisting of
(2A) moieties (i) in which b is a bond, (ii) which have the formula —Cy and (iii) which are directly linked to the terminal —CO—O— moiety of one of the repeating units having formula (1),
(2B) moieties (i) in which b is a moiety having the formula —O—CO—, (ii) which have the formula —O—CO—Cy and (iii) which are directly linked to the terminal —CF$^1$F$^2$— moiety of one of the repeating units having formula (1), and
(2C) moieties (i) in which b is a moiety having the formula -R$_{pbalc}$—CO—, (ii) which have the formula -R$_{pbalc}$—CO—Cy, where R$_{pbalc}$ is the residue of a polyol, and (iii) which are directly linked to the terminal -0CO—O— moiety of one of the repeating units having formula (1);
(2) the polymer has a crystalline melting temperature, Tp, of at least 40° C., an onset of melting temperature, To, such that the value of (Tp–To) is less than 10° C., and a heat of fusion of at least 5 J/g; and
(3) the polymer has a number average molecular weight, Mn, of less than 8,000.

10. A formulation according to claim 9 wherein the polymer has molecular weight less than 5000.

11. A formulation according to claim 9 wherein the polymer contains 2-30 molar percent of the terminal units.

12. A formulation according to claim 9 wherein the polymer contains 10-40% by weight of Cy moieties.

13. A formulation according to claim 9 wherein Cy consists of an n-alkyl moiety containing 22 carbon atoms.

14. A formulation according to claim 9 wherein at least one of the terminal units of formula (2) has a formula selected from the group consisting of —CH$_2$—CH(OH)—CH$_2$—O—CO-Cy and —CH$_2$—CH(O—CO—Cy)—CH$_2$—O—CO—Cy wherein the Cy moiety consists of an n-alkyl moiety containing 18-24 carbon atoms.

15. A formulation according to claim 9 wherein at least some of the polymeric molecules contain at least three Cy moieties.

16. A formulation according to claim 9 wherein the polymer contains less than 170 repeating units of the formulas (1A) and (1B).

17. A formulation according to claim 1 wherein the drug is selected from the group consisting of proteins, polypeptides and small molecule drugs.

18. A formulation according to claim 9 wherein the drug is a protein or a polypeptide.

19. A formulation according to claim 9 wherein the drug is a small molecule drug.

20. A pharmaceutical formulation comprising a drug and a polymer, wherein
(1) the polymer comprises a plurality of polymeric molecules each of which consists essentially of
(i) a polymer backbone which comprises a plurality of repeating units having the formula

—CF$^1$F$^2$—CO—O— wherein
F$^1$ is hydrogen and F$^2$ is hydrogen or methyl, the repeating units being the same or different, and
(ii) at least one terminal unit which has the formula wherein
Cy consists of an n-alkyl moiety containing 18-24 carbon atoms, and
b is a bond or a moiety which has a valence of at least 2 and which links the Cy moiety to the polymer backbone;
(2) the polymer has a crystalline melting temperature, Tp, of at least 40° C., an onset of melting temperature, To, such that the value of (Tp–To) is less than Tp$^{0.7}$, and a heat of fusion of at least 5 J/g;
(3) the polymer has a number average molecular weight, Mn, of less than 10,000; and
(4) the polymer is the reaction product of starting materials consisting of
(i) a preformed polymer which comprises a plurality of repeating units having the formula (1) and which has a terminal carboxyl group, and
(ii) an alcohol containing said Cy moiety.

21. A formulation according to claim 20 wherein the preformed polymer has the formula HO—(—CF$^1$F$^2$—CO—O—)$_n$—H where n is an integer less than 170.

22. A formulation according to claim 20 wherein the preformed polymer was prepared by the polymerization of lactide and glycolide.

23. A formulation according to claim 20 wherein the preformed polymer was prepared by the polymerization of lactic and glycolic acids.

24. A formulation according to claim 20 wherein the reaction product has a number average molecular weight less than 5000.

25. A formulation according to claim 20 wherein the Cy moiety consists of an n-alkyl moiety containing 22 carbon atoms.

26. A formulation according to claim 20 wherein the drug is a protein, polypeptide, or a small molecule drug.

27. A pharmaceutical formulation comprising a drug and a polymer wherein which
(1) the polymer comprises a plurality of polymeric molecules each of which consists essentially of
(i) a polymer backbone which comprises a plurality of repeating units having the formula

—CF$^1$F$^2$—CO—O—     (1)

wherein
F$^1$ is hydrogen and F$^2$ is hydrogen or methyl, the repeating units being the same or different, and
(ii) at least one terminal unit which has the formula -b—Cy     (2)

wherein
Cy consists of an n-alkyl moiety containing 18-14 carbon atoms, and
b is a bond or a moiety which has a valence of at least 2 and which links the Cy moiety to the polymer backbone;
(2) the polymer has a crystalline melting temperature, Tp, of at least 40° C., an onset of melting temperature, To, such that the value of (Tp–To) is less than Tp$^{0.7}$, and a heat of fusion of at least 5 J/g;
(3) the polymer has a number average molecular weight, Mn, of less than 10,000; and
(4) the polymer is the reaction product of starting materials consisting of (i) a preformed polymer which comprises a plurality of repeating units having the formula (1) and which has a terminal hydroxyl group, and
(ii) a carboxylic acid, acid chloride or anhydride containing said Cy moiety.

28. A formulation according to claim 27 wherein the preformed polymer has the formula HO—(—CF$^1$F$^2$—CO—O—)$_n$—H where n is an integer less than 170.

29. A formulation according to claim 27 wherein the preformed polymer was prepared by the polymerization of lactide and glycolide.

30. A formulation according to claim 27 wherein the preformed polymer was prepared by the polymerization of lactic and glycolic acids.

31. A formulation according to claim 27 wherein the reaction product has a number average molecular weight less than 5000.

32. A formulation according to claim 27 wherein the Cy moiety consists of an n-alkyl moiety containing 22 carbon atoms.

33. A formulation according to claim 27 wherein the drug is a protein, a polypeptide or a small molecule drug.

34. A pharmaceutical formulation comprising a drug and a polymer, wherein
(1) the polymer comprises a plurality of polymeric molecules each of which consists essentially of
(i) a polymer backbone which comprises a plurality of repeating units having the formula

—CF$^1$—F$^2$—CO—O—  (1)

wherein
F$^1$ is hydrogen and F$^2$ is hydrogen or methyl, the repeating units being the same or different, and
(ii) at least one terminal unit which has the formula -b—Cy  (2)

wherein
Cy consists of an n-alkyl moiety containing 18-24 carbon atoms, and
b is a bond or a moiety which has a valence of at least 2 and which links the Cy moiety to the polymer backbone;
(2) the polymer has a crystalline melting temperature, Tp, of at least 40° C., an onset of melting temperature, To, such that the value of (Tp−To) is less than Tp$^{0.7}$, and a heat of fusion of at least 5 J/g;
(3) the polymer has a number average molecular weight, Mn, of less than 10,000; and
(4) the polymer is the reaction product of a method which comprises the steps of
(A) reacting
(i) a preformed polymer which comprises a plurality of repeating units having the formula (1) and which has a terminal carboxyl group, and
(ii) a polyol, and
(B) reacting the product of step (A) with a carboxylic acid, acid chloride or anhydride containing said Cy moiety.

35. A formulation according to claim 34 wherein the preformed polymer has the formula HO—(—CF$^1$F$^2$—CO—O—)$_n$—H where n is an integer less than 170.

36. A formulation according to claim 34 wherein the preformed polymer was prepared by the polymerization of lactide and glycolide.

37. A formulation according to claim 34 wherein the preformed polymer was prepared by the polymerization of lactic and glycolic acids.

38. A formulation according to claim 34 wherein the reaction product has a number average molecular weight less than 5000.

39. A formulation according to claim 34 wherein the Cy moiety consists of an n-alkyl moiety containing 22 carbon atoms.

40. A formulation according to claim 34 wherein the drug is a protein, a polypeptide or a small molecule drug.

* * * * *